United States Patent [19]

Stankiewicz

[11] Patent Number: 4,568,284
[45] Date of Patent: Feb. 4, 1986

[54] DENTAL HANDPIECE

[75] Inventor: Stanley L. Stankiewicz, Chicago, Ill.

[73] Assignee: Sybron Corporation, Rochester, N.Y.

[21] Appl. No.: 665,452

[22] Filed: Oct. 26, 1984

[51] Int. Cl.[4] .............................................. A61C 1/08
[52] U.S. Cl. ...................................... 433/126; 433/29
[58] Field of Search ................................. 433/126, 29

[56] References Cited

U.S. PATENT DOCUMENTS 4,504,227 3/1985 Lohn .................................. 433/126
4,507,085 3/1985 Mosimann et al. ................. 433/126

FOREIGN PATENT DOCUMENTS 1068425 5/1959 Fed. Rep. of Germany .

Primary Examiner—Robert Peshock
Attorney, Agent, or Firm—Robert A. Gerlach; Robert J. Bird

[57] ABSTRACT

A dental handpiece including motor portion and swivelable attachment portion. The motor portion includes an annular electrical commutator on its end facing the attachment. The attachment includes a lamp and associated electrical contacts for swivel contact with the commutator. The lamp illuminates the handpiece work area, either directly or through optical fibers. Swivelable chip air and water conduits in the motor/attachment combination are also disclosed.

3 Claims, 7 Drawing Figures

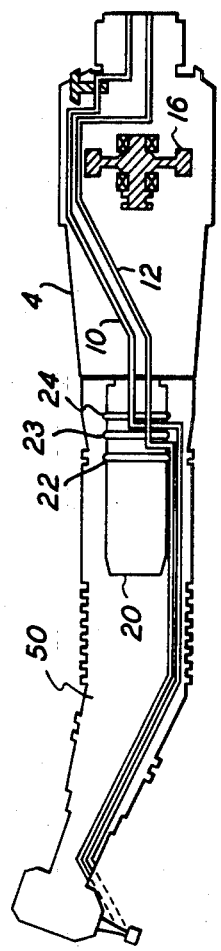
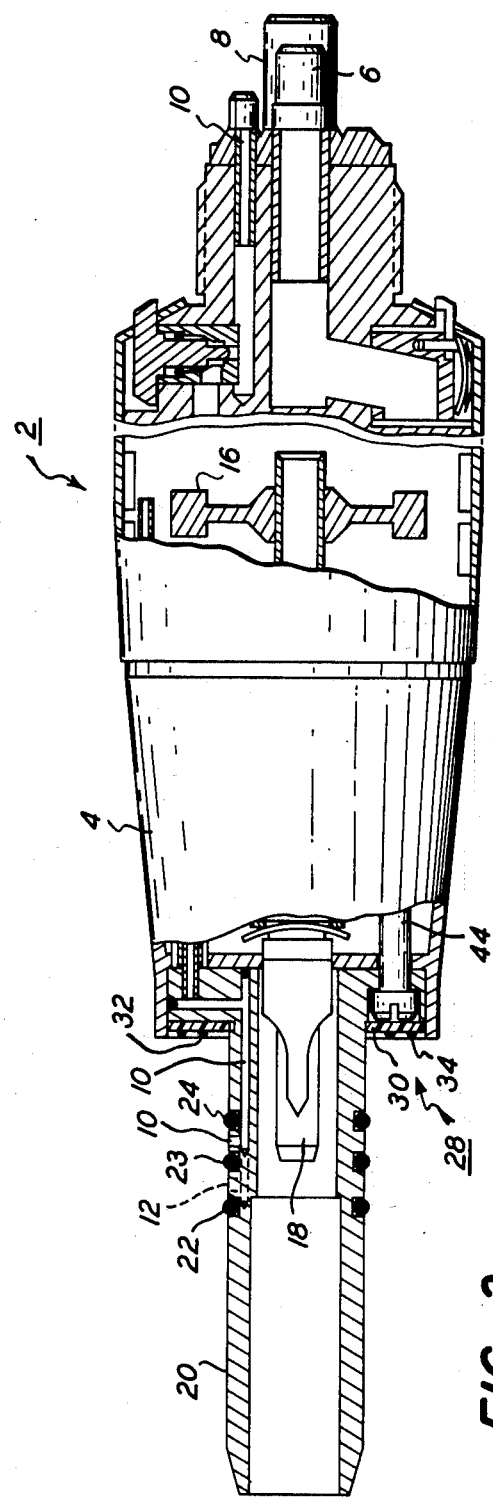
PRIOR ART
FIG. 1
FIG. 2

DENTAL HANDPIECE

BACKGROUND AND SUMMARY OF THE INVENTION

The subject matter of this invention is a dental handpiece having provision for swiveling about its axis, illumination of its work area, and the delivery of water and air to the work area.

The most relevant prior art that I know of is the AM-40 handpiece manufactured and sold by the Ritter-Midwest division of Sybron Corporation, the assignee of the present invention. The AM-40 handpiece is illustrated and described in advertising literature entitled *The AM-40 Multi-Speed System* accompanying this application. A brief reference to this accompanying literature, in particular the diagram of the handpiece described therein, will serve as convenient background to the present invention. The handpiece is shown there as having two major components: a handpiece motor shown in gray and a handpiece attachment shown only in outline and attached to the motor. The male connector portion of the motor fits within the attachment and is sealed relative to the attachment by three O-rings which define a pair of annular flow channels, one for chip air and one for water. The attachment is swivelable relative to the motor and the annular channels permit the continuous flow of chip air and water from the motor casing to the attachment regardless of angular displacement or swiveling of the attachment.

To this prior art, the present invention adds provision for light transmission to the work area. This is accomplished by means of electrical energy delivered to an annular commutator disposed on the motor housing at the swivel interface between motor housing and handpiece attachment. The handpiece attachment in turn includes an electric lamp with a removable base in sliding contact with the commutator. The lamp illuminates an optical fiber bundle which extends from the lamp to the head end of the attachment for illumination of the work area.

DRAWINGS

FIG. 1 is a simplified and somewhat schematic side view of a prior art handpiece as described above.

FIG. 2 is a side view, partly in section along line II—II of FIG. 3, of a handpiece motor in accordance with this invention.

Figure 3:
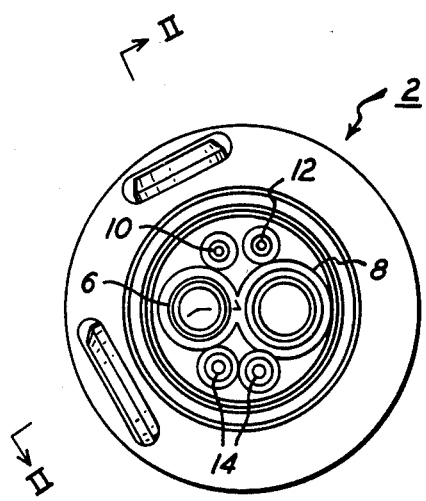
FIG. 3 is a right end view of the motor of FIG. 2.
Figure 4:
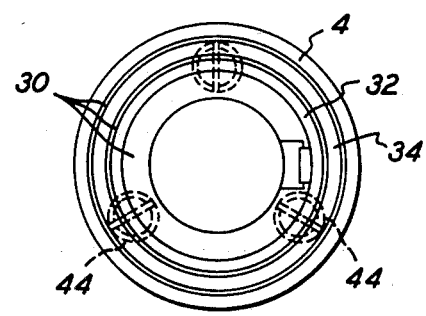
FIG. 4 is a simplified left end view of the motor of FIG. 2.
Figure 7:
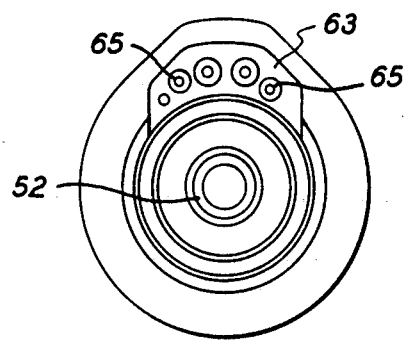
FIG. 7 is a simplified right end view of the handpiece attachment of FIG. 6.
Figure 5:
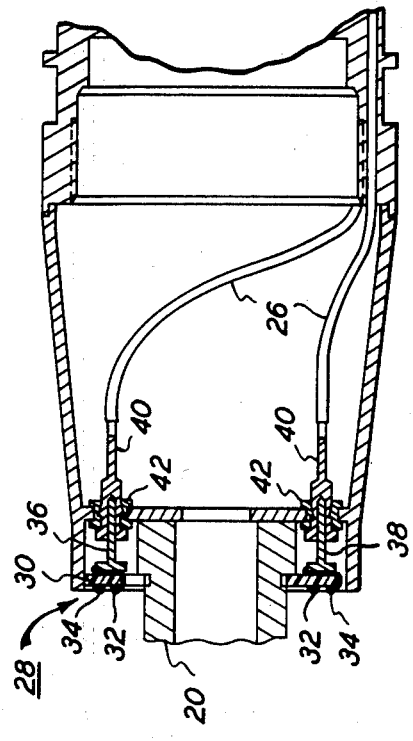
FIG. 5 is a simplified partial side section of the handpiece motor of FIG. 2, rotated somewhat relative to FIG. 2.

In all these views, certain elements are simplified and much detail unnecessary to an understanding of the present invention is omitted.

DESCRIPTION

In FIG. 1, a prior art handpiece is represented and includes a motor housing 4 from which extends a cylindrical connector member 20 for mating engagement within a handpiece attachment 50. O-rings 22, 23 and 24 around the cylindrical connector 20 form a sealing engagement between connector 20 and attachment 50, and provide separate passages for the flow of water and chip air, along flow paths 10 and 12 respectively, from motor housing 4 to handpiece attachment 50 for discharge at the head end of the handpiece onto the work area. Attachment 50 is swivelable relative to the motor housing 4.

The foregoing is a summary description of the prior art. FIGS. 2-7 in which the improvement of this invention is described, use the same reference numerals for like elements.

In FIGS. 2, 3, 4 and 5 a handpiece motor is generally indicated at 2 and includes a motor housing 4 adapted at its right end for attachment to a supply hose, not shown. At the hose end of the motor housing 4, are conduits or passages for turbine drive air 6, turbine exhaust air 8, water 10, chip air 12 and electrical connections 14, all of which mate with corresponding conduits in the supply hose. Air passages 6 and 8 carry air respectively to and from a turbine motor 16 suitably mounted within the motor housing 4. A drive spindle 18 extends axially from the turbine motor for connection to a drive assembly, transmission, and ultimately to the handpiece head for rotation of a tool, bur, or the like. A connector member 20 extends from the left end of the motor housing 4, surrounding the drive spindle 18, and is adapted for insertion into a handpiece attachment in sealing engagement therewith by means of O-rings 22, 23, and 24.

The water passage 10 extends through the motor housing 4 and the body of the connector member 20, from which it discharges between O-rings 23 and 24. Similarly, the chip air passage 12 extends throught the motor housing 4 and the connector member 20 from which it discharges between O-rings 22 and 23. Electrical connections 14 lead through suitable wiring 26 within the motor housing 4 to an annular commutator ring 28 mounted at the left end of the motor housing and facing the handpiece attachment 50. Commutator 28 includes an insulative support ring 30 which supports an inner and an outer conductive ring 32 and 34. Inner ring 32 is electrically connected as by soldering to a connecting pin 36 and outer ring 34 is similarly electrically connected to connecting pin 38. Commutator 28 is detachably mounted to the motor housing 4 by the insertion of pins 36 and 38 into mating spring loaded conductive contacts 40 which are mounted on motor housing 4 by insulative bushings 42. Spring loaded contacts 40 are each connected to one of the wires 26 which in turn connect to electrical connections 14. Behind the commutator 28 is one or more assembly screws 44 holdng the motor housing 4, connector 20 and turbine motor 16 together. These assembly screws are easily accessible for disassembly of the entire handpiece motor by the simple removal of the commutator 28.

Figure 6:
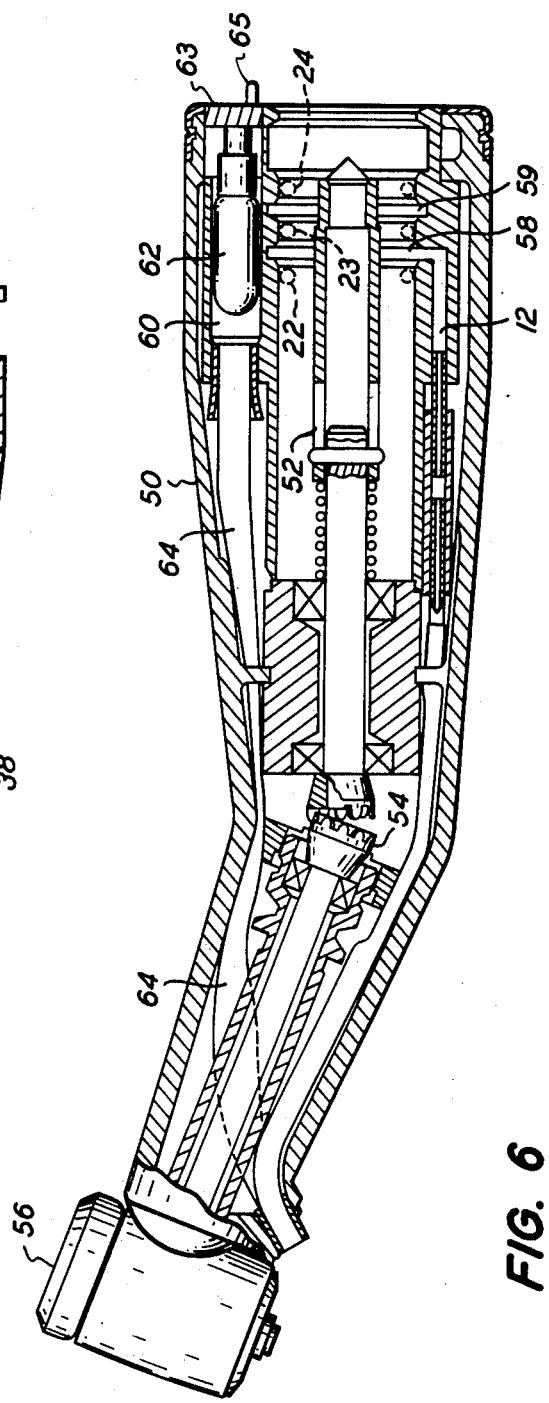
FIG. 6 is a side view, partly in section, of a handpiece attachment according to this invention.

As stated earlier, the handpiece motor assembly 2, shown in FIG. 2, is adapted for mating engagment with a handpiece attachment, generally indicated at 50 in FIG. 6. When these two components are joined, the O-rings 22, 23, and 24 in FIG. 2 are located in the positions shown in phantom in FIG. 6.

The handpiece attachment 50 in FIG. 6, as is well-known, includes within it a drive assembly 52 and transmission 54 for delivery of rotary motion to the head 56 which is typically at right angles to the transmission and includes a chuck for the mounting of a working tool, bur or the like. The right end of the handpiece attachment 50 includes a generally cylindrical cavity into which is inserted the connector 20 for the connection of motor drive spindle 18 with the drive assembly 52.

The interior of the handpiece attachment 50 includes a pair of annular channels 58, 59. Annular channel 58, between O-rings 22 and 23, communicates with the air passage 12 in the motor housing 4 and with its continuation in the handpiece attachment 50 through which it extends to its point of discharge near the working end of the handpiece. Similarly, the other annular channel 59, between O-rings 23 and 24, communicates with water passage 10 in the motor housing and with its continuation in the handpiece attachment to a point of discharge at the head end of the handpiece adjacent that of the air passage. When the handpiece motor 2 is connected to the handpiece attachment 50, that is when the connector 20 is placed inside the open end of the attachment 50, it will be seen that the O-rings 22, 23 and 24 form a seal with the interior of the attachment and isolate the air annular channel 58 and the water annular channel 59 and therefore create substantially fluid tight seals on each side of these annuli.

Handpiece attachment 50 includes a lamp cavity 60 into which a lamp 62 extends. Lamp 62 is removably attached to a base 63 with commutator brushes 65 which are in turn positioned for contact with the commutator 28 when the handpiece motor and attachment are joined. Lamp cavity 60 leads to the face of an optical fiber bundle 64 which extends from the lamp to the head end of the handpiece attachment where it terminates, adjacent the air and water outlets, for illumination of the work area. Lamp base 63 and commutator 28 maintain electrical contact while the attachment 50 is swivelable relative to the motor housing 4. An alternative arrangement omits the fiber bundle 64, places the lamp 62 at the head end of the instrument, and extends electrical wires from the points of contact with commutator 28 to the lamp.

The handpiece motor described herein is preferably of size and dimension such that any standard International Standards Organization (ISO) handpiece attachment is usable with it, whether or not the attachment is provided with a lamp or flow passages. Of course, all the benefits of chip air, water, and illumination will be realized only with attachments providing for the extension of these services. But for power transmission to the head, any ISO handpiece attachment may be used.

While the motor of this invention has been described as including an air turbine, it is also contemplated that an electric motor or vane motor may be used instead of the air turbine as the prime mover element.

What is claimed is:

1. A dental handpiece motor adapted for connection at one end thereof to a source of air, water, and electrical energy and for swivel connection at the other end thereof to a handpiece attachment, said motor including a housing (4) supporting a rotor and defining passages for transmission of chip air and water from said source to said handpiece attachment, said motor further including first and second electrical conductors (26) adapted for connection to said source, a removable electrical commutator unit (28) disposed on the end of said motor housing facing said handpiece attachment for providing electrical continuity to said attachment, said commutator unit including:,
 a. an insulative support ring (30),
 b. inner and outer concentric conductive rings (32, 34) supported on said support ring,
 c. a first connecting pin (36) electrically connected to and extending axially from said inner conductive ring (32),
 d. A second connecting pin (38) electrically connected to and extending axially from said outer conductive ring (34),
 e. a mating contact (40) electrically connected to each of said conductors (26),
 f. said connecting pins (36, 38) being in releasable frictional engagement with said mating contacts (40), whereby said commutator unit (28) is removably connected with said motor.

2. A dental handpiece including a motor (2) and an attachment (50) swivelably connected to said motor;
said motor being adapted for connection at one end thereof to a source of air, water, and electrical energy; said motor including a housing (4) supporting a rotor and defining passages for transmission of chip air and water from said source to said attachment; said motor further including first and second electrical conductors (26) adapted for connection to said source, and an electrical commutator unit (28) disposed on the end of said motor housing facing said attachment for providing electrical continuity to said attachment; said commutator unit including an insulative support ring (30) and inner and outer concentric conductive rings (32, 34), said conductive rings respectively releasably frictionally engaging said first and second electrical conductors (26), said commutator unit being thereby removably connected to said motor housing;
said attachment (50) defining a lamp cavity (60) in which is removably disposed a lamp (62) mounted on a separable lamp base (63), said lamp base including commutator brushes (65) disposed for sliding contact with said commutator (28).

3. A dental handpiece as defined in claim 2 in which said attachment (50) further includes a light guide extending within said attachment from said cavity (60) to the end of said attachment adjacent said work area.

* * * * *